United States Patent
Berghs et al.

(10) Patent No.: US 9,931,147 B2
(45) Date of Patent: Apr. 3, 2018

(54) ARTICULAR FRACTURE FIXATION SYSTEM AND METHOD

(71) Applicants: UNIVERSITEIT GENT, Ghent (BE); Bart Berghs, Snellegem (BE)

(72) Inventors: Bart Berghs, Snellegem (BE); Lieven De Wilde, Ghent (BE)

(73) Assignee: Universiteit Gent, Ghent (BE)

( * ) Notice: Subject to any disclaimer, the term of this patent is extended or adjusted under 35 U.S.C. 154(b) by 368 days.

(21) Appl. No.: 14/651,315

(22) PCT Filed: Dec. 13, 2013

(86) PCT No.: PCT/EP2013/076495
§ 371 (c)(1),
(2) Date: Jun. 11, 2015

(87) PCT Pub. No.: WO2014/090979
PCT Pub. Date: Jun. 19, 2014

(65) Prior Publication Data
US 2015/0366594 A1  Dec. 24, 2015

(30) Foreign Application Priority Data

Dec. 14, 2012  (EP) .................................. 12197239

(51) Int. Cl.
*A61B 17/80*  (2006.01)

(52) U.S. Cl.
CPC ........ *A61B 17/8033* (2013.01); *A61B 17/809* (2013.01); *A61B 17/8061* (2013.01)

(58) Field of Classification Search
CPC ....... A61B 17/74; A61B 17/742; A61B 17/80; A61B 17/8004

(Continued)

(56) References Cited

U.S. PATENT DOCUMENTS 8,911,482 B2 * 12/2014 Lee .................... A61B 17/8057
606/286
2008/0147203 A1  6/2008 Cronin et al.
(Continued)

FOREIGN PATENT DOCUMENTS

FR  2 738 739 A1  3/1997

OTHER PUBLICATIONS

PCT Notification Concerning Transmittal of International Preliminary Report on Patentability and Written Opinion of the International Searching Authority dated Jun. 25, 2015 in connection with PCT International Patent Application No, PCT/EP2013/076495, 9 pages.

(Continued)

*Primary Examiner* — Ellen C Hammond
*Assistant Examiner* — Christina Negrellirodriguez
(74) *Attorney, Agent, or Firm* — Amster, Rothstein & Ebenstein LLP

(57) ABSTRACT

Provided herein is an osteosynthesis device for articular fracture fixation, more particularly for fixation of shoulder, knee, elbow, ankle and wrist fractures. The osteosynthesis device comprises an articular supportive plate for supporting the articular surface of a long bone, said articular supportive plate comprising (i) at least one pin receiving feature for receiving a pin or a screw; and (ii) at least one fin projecting from a first side of said articular supportive plate, said fin being provided with one or more pin receiving features for receiving a pin or screw. Further provided herein are systems for articular fracture fixation, and methods of fixating an articular fracture in a long bone using such systems.

16 Claims, 13 Drawing Sheets

(58) Field of Classification Search
USPC ............... 606/62–68, 280–299, 86 R, 87–89
See application file for complete search history.

(56) References Cited

U.S. PATENT DOCUMENTS

| | | |
|---|---|---|
| 2011/0029025 A1 | 2/2011 | Medoff |
| 2011/0306976 A1 | 12/2011 | Kubiak et al. |
| 2012/0150240 A1 | 6/2012 | Medoff |
| 2014/0121709 A1* | 5/2014 | Gonzalez-Hernandez A61F 2/4261 606/286 |

OTHER PUBLICATIONS

PCT International Search Report dated Mar. 13, 2014 in connection with PCT International Patent Application No. PCT/EP2013/76495, 6 pages.

* cited by examiner

ARTICULAR FRACTURE FIXATION SYSTEM AND METHOD

CROSS-REFERENCE TO RELATED APPLICATIONS

This application is a U.S. national stage entry under 35 U.S.C. § 371 of PCT International Patent Application No. PCT/EP2013/076495, filed Dec. 13, 2013, which claims priority to European Patent Application No. 12197239.2, filed Dec. 14, 2012, the contents of all of which are incorporated herein by reference in their entirety.

FIELD OF THE INVENTION

Provided herein are devices and systems for articular fracture fixation, more particularly for fixation of shoulder, knee, elbow, ankle or wrist fractures. Further provided are methods of fixating an articular fracture using such devices and systems.

BACKGROUND OF THE INVENTION

Articular fractures, and more particularly proximal humeral fractures, are a frequent event often seen in elderly patients, and comprise about 5% of all fractures. Although many proximal humeral fractures are stable injuries which can be treated non-operatively, surgical intervention is required in about 20% of all cases, particularly with complex fractures. However, complex fractures of the proximal humerus are notoriously difficult to manage, particularly in elderly patients. Indeed, internal fixation is difficult because of the small size of the bone fragments and the quality of the bone stock is often poor due to osteoporosis. In addition to these mechanical problems, there further is a risk of avascular necrosis of the humeral head (caput humeri).

Various devices and systems for proximal humeral fracture fixation are known in the art, including locking plates, intramedullary rods, and the so-called Bilboquet device.

Locking plates such as proximal humeral fixation plates are typically made from stainless steel or titanium, and are locked onto the bone via screws, thereby providing stability. However, especially in case of osteoporotic bone, the relatively long screws, situated in the subchondral plate to enhance stability may perforate the caput humeri completely, and cause damage to the glenoid cavity. Moreover, locking plates may provide for fixation, but do not provide for sufficient stability in all cases. This is particularly problematic in proximal humeral fractures with a varus deformity or metaphysial comminution.

Implants such as intramedullary rods share the load with the bone, rather than entirely supporting the bone. However, these implants may cause enlargement of the fracture and/or iatrogenic complications in the subacromial space. Moreover, the possibilities for fixation of complex fractures are limited.

The Bilboquet device (described in patent FR2669528) is a two-part implant consisting of a circular staple which is impacted into the articular surface of the caput humeri, and a diaphyseal stem that inserts into a cup provided onto the staple. However, the position of the staple in the caput humeri is difficult to adjust during surgery, and the implantation of the device into the bone requires an expansion of the fracture. Moreover, the limited number of implant models limits the amount possibilities for the surgeon. Similar problems occur with other articular fractures.

There is therefore a need for methods and systems for fixation of complex articular fractures which mitigate at least one of the problems stated above.

SUMMARY OF THE INVENTION

Provided herein are devices and systems for articular fracture fixation, and methods of fixating an articular fracture in long bones using such devices and systems. Although the devices, kits and methods are described herein mostly with respect to proximal humeral joint fracture fixation, these devices and systems may, mutatis mutandis, also be used for fixation of other joint fractures, such as knee fractures (distal femoral fractures and/or tibial plateau fractures), elbow fractures (distal humeral fractures), wrist fractures (distal radial fractures) and ankle fractures (pilon fractures) (see Table 1).

In a first aspect, the invention provides an osteosynthesis device for articular fracture fixation, comprising an articular supporting plate for supporting an articular surface of a long bone, said articular supportive plate comprising:

a first side, for orienting centromedullarly facing the cancellous bone and a second side for facing or supporting the articular surface, said first side comprising at least one pin receiving feature for receiving a pin or a screw; and at least one fin attached to or attachable to said articular supportive plate; wherein, when attached to said articular supportive plate, said fin projects from a first side of said articular supportive plate, said fin further being provided with one or more pin receiving features for receiving a pin or screw. In preferred embodiments, said fin is provided with a plurality of pin receiving features.

Preferably, the pin receiving feature provided on the articular surface and the pin receiving features provided on the fin(s) allow for receiving screws or pins from more than one direction.

In a preferred embodiment of the osteosynthesis device according to the invention, said articular supportive plate comprises:

one fin attached to or attachable to said articular supportive plate wherein, when attached to said articular supportive plate, said fin projects from said plate, preferably from a central part thereof; or two or more fins attached to or attachable to said articular supportive plate wherein, when attached to said articular supportive plate, said fins project from said plate; preferably from lateral parts of said supportive plate.

In particular embodiments, the pin receiving features provided on the articular supportive plate provide a plurality of upstanding rods, plugs or fingers, protruding from said supportive plate.

In a further preferred embodiment of the osteosynthesis device according to the invention, one edge of said articular supportive plate is further provided with an upstanding tab.

In a further preferred embodiment of the osteosynthesis device according to the invention, said one or more pin receiving features of said articular supportive plate are configured to receive a variable angle locking screw.

In a further preferred embodiment of the osteosynthesis device according to the invention, the outer dimensions of the articular supportive plate can be between about 2 and 5 cm, preferably between 2 and 3 cm, and/or can have a thickness of between about 1 and 5 mm, preferably between about 1 and 4 mm, more preferably between about 1 and 3 mm.

The invention further provides a kit comprising the osteosynthesis device according to any one of the above embodiments, and further comprising a diaphyseal plate, said diaphyseal plate comprising:
- a longitudinal distal plate portion provided with at least one through hole for securing said diaphyseal plate to the shaft of the long bone; and
- a proximal plate portion provided with at least one through hole, wherein said through hole of said proximal plate portion and at least one of said holes of said articular supportive plate or fin are configured to respectively send and receive the same screw or pin.

In a preferred embodiment, the kit according to the present invention, further comprises at least one containment plate provided with one or more through holes, wherein said containment plate and said proximal plate portion each comprise an adjustable coupling feature for coupling said containment plate to said proximal plate portion.

In a further preferred embodiment of the kit according to the present invention, said coupling features provide a rail system. Preferably, said containment plate is flexible or malleable.

In a further embodiment of the kit according to the present invention, said articular supportive plate and said diaphyseal plate are formed of one or more materials selected from the group consisting of titanium, titanium alloy, cobalt-chromium alloy, stainless steel, tantalum, tantalum alloy, polyethylene, polyether ether ketone, poly(lactic acid), poly(D-lactic acid), poly (L-lactic acid), poly(glycolic acid), poly(ε-caprolactone), poly(dioxanone), poly(lactide-co-glycolide), polypropylene fumarate) (PPF), oligo(poly(ethylene glycol) fumarate), poly(glycolide-co-trimethylene carbonate), a polyorthoester, a polyether ether ketone (PEEK) and a polyanhydride.

In a further embodiment, the kit according to the present invention, further comprises at least one screw, said screw being cuttable or breakable, or adjustable in length. Preferably, said screw is formed from one or more biocompatible polymers.

In a further embodiment of the kit according to the present invention, at least one of said through holes provided on said articular supportive plate, diaphyseal plate or containment plate comprises a stopping feature. Alternatively, the stopping feature can be present on the screws, e.g. by providing a non-threaded part, preventing the user from inserting the screw too deep in the articular supportive plate.

In a further embodiment of the kit according to the present invention, said articular supportive plate and diaphyseal plate comprise a hydroxyapatite coating.

The invention further provides for the use of the device or kit according to any one of the embodiments defined herein, for repairing a fracture selected from the group consisting of: the proximal humerus, the proximal or distal radius, the proximal or distal tibia, and the distal femur.

The invention further provides a method of fixating or repairing an articular fracture using the kit according to any one of the aspects defined above, said method comprising:
(a) mounting of said articular supportive plate under the articular surface of the proximal or distal end of the bone;
(b) securing said diaphyseal plate to the shaft of the bone;
(c) reducing the fracture;
(d) locking the relative position of said articular supportive plate and said diaphyseal plate via one or more screws or pins; and
(e) optionally, coupling one or more containment plates onto said diaphyseal plate, and securing said containment plates onto said distal or proximal end of the joint bone.

In particular embodiments, said method is used for repairing a fracture selected from the group consisting of: the proximal humerus, the proximal or distal radius, the proximal or distal tibia, and the distal femur.

The invention further provides an osteosynthesis device for proximal humeral fracture fixation, comprising an articular supportive plate for supporting the caput humeri of a humerus. The articular supportive plate comprises at least one fin attached to or attachable to said articular supportive plate. When attached to said articular supportive plate, the fin projects from a first side of the articular supportive plate. The fin is further provided with one or more means or holes for receiving a pin or screw.

The independent and dependent claims set out particular embodiments envisaged herein. Features from the dependent claims may be combined with features of the independent or other dependent claims as appropriate.

The use of the devices and systems described herein may significantly facilitate reduction of the fracture, and may reduce the risk of damaging the bone during reduction. Moreover, the devices and systems described herein may allow for the use of relatively short screws, thereby reducing the risk of perforation of the caput humeri and potential resulting glenoid cavity damage. Moreover, the combination of a diaphyseal plate with an articular supportive plate as described herein may provide an increased stability. The systems described herein do not require the use of intramedullary rods or a diaphyseal stem, and may further provide an increased flexibility for fixation of complex fractures, e.g. for fixation of tuberosities, tubercles, malleoli, styloid processes or other bulbous processes of the respective bone surfaces referred herein.

The above and other characteristics, features and advantages of the concepts described herein will become apparent from the following detailed description, which illustrates, by way of example, the principles of the invention.

BRIEF DESCRIPTION OF THE DRAWINGS

The drawings depicted herein are merely for illustrative purposes and are not to be seen as limiting the invention in any particular way.

DETAILED DESCRIPTION OF THE INVENTION

Figure 1A:
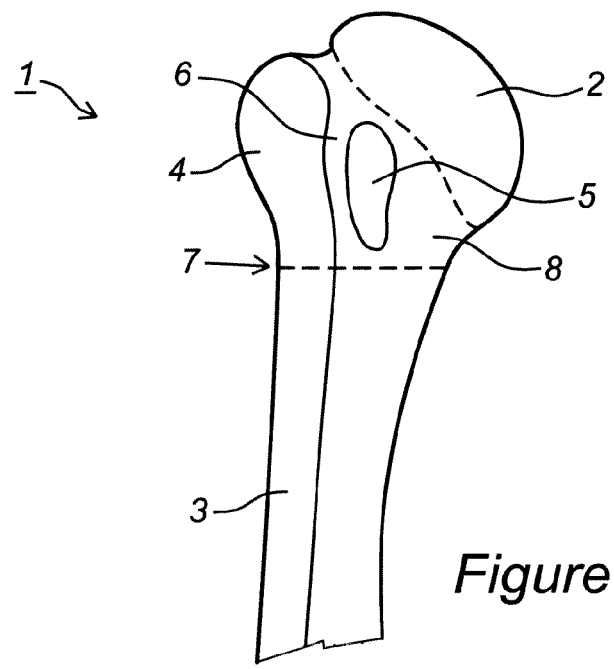
FIG. 1: Schematic view of the proximal humerus (1): (a): intact proximal humerus (1), showing the humerus head or caput humeri (2) affixed to the diaphysis (3). The two tuberosities (greater tuberosity (4) and lesser tuberosity (5)) are also depicted on the humeral head, and are divided by the intertubercular groove (6). The dotted line indicates the surgical neck (7) and anatomical neck (8) of the humerus; (b): a single fracture (9) of the proximal humerus, wherein the head (2) of the humerus is broken from the diaphysis (3) at the surgical neck; (c): a complex multiple fracture (9) scheme, wherein the greater and lesser tuberosities (4, 5)) are also detached from the humeral head (2); (d): a transverse schematic of the fracture of (b), from an osteoporotic subject, wherein the humeral head (2) is partially hollow or porous (10), and only a roman arch (11) form remains of more or less solid bone, called the articular surface.
Figure 1B:
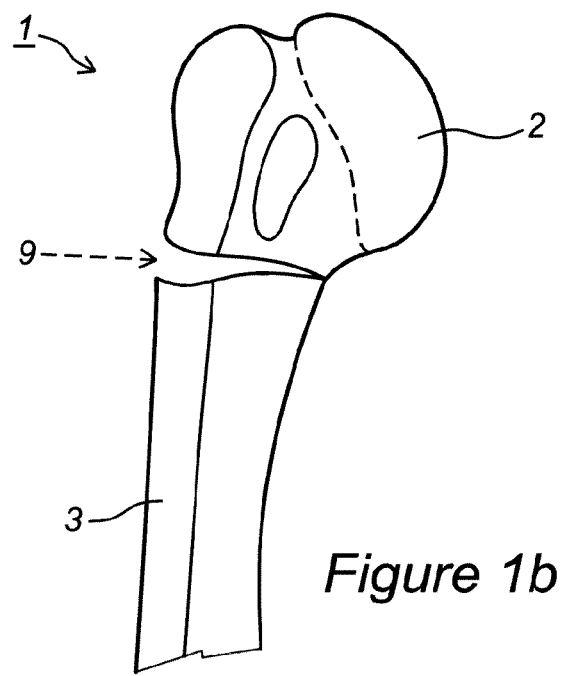
Figure 1C:
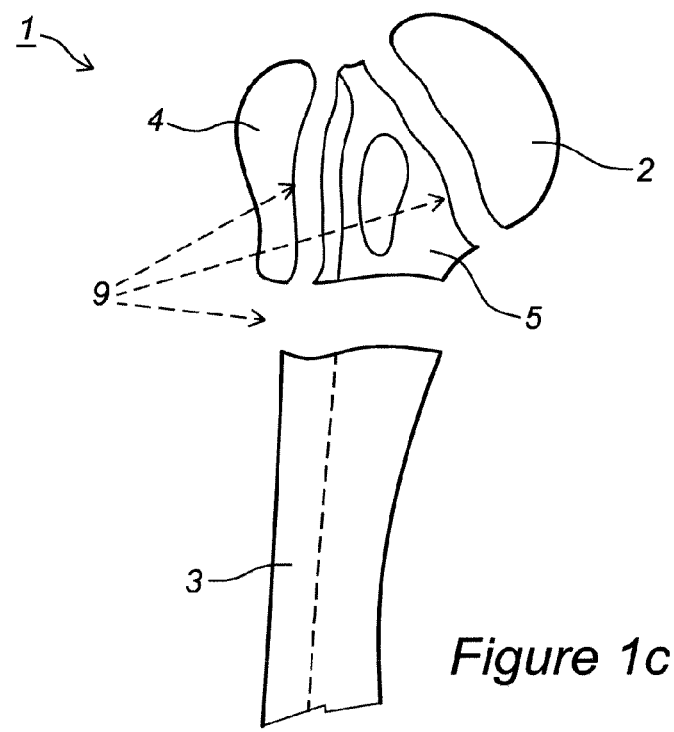
Figure 1D:
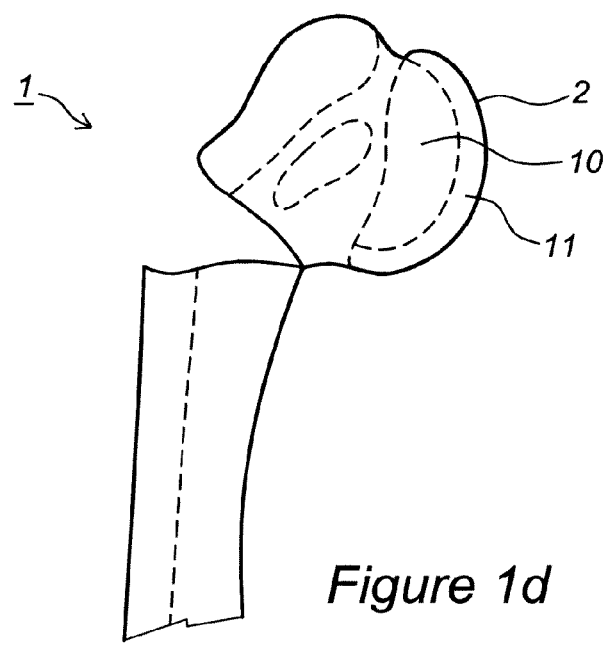

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to ensure one or more of the technical effects envisaged herein. The term "about", used in combination with numerical values is to be interpreted in the light of said variation. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

The term "long bone" as used herein refers to bones of the human or animal body that are longer than they are wide. Long bones grow primarily by elongation of the diaphysis (also referred to herein as "shaft"), with an epiphysis at each end of the growing bone. The ends of epiphyses are typically covered with hyaline cartilage, also known as "articular cartilage". More particular, in human patients, the term "long bone" refers to a bone selected from the list consisting of a humerus, a femur, a tibia, and a radius.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Provided herein are devices and systems for articular fracture fixation, for example proximal humeral fracture fixation, in a human or animal patient. In preferred embodiments, the patient is a human patient. In a first aspect, provided herein is an osteosynthesis device for articular fracture fixation. The osteosynthesis device described herein comprises an articular supportive plate, also referred to herein as "supportive plate", for supporting the articular surface of a long bone, for example the caput humeri of a humerus. The articular supportive plate (12) has opposing first (13) and second (14) sides (see FIG. 4).

The second side of the articular supportive plate faces the articular surface of the long bone and is used for mounting the articular supportive plate under the articular surface of the long bone, for example the caput humeri of a humerus. More particularly, when the supportive plate is mounted under the articular surface of the long bone, the second side of the supportive plate contacts the articular surface. The first side of the articular plate, which is on the opposite side of the second side, has one or more fin(s) (15) oriented towards the centromedullar region of the long bone. The first side of the articular plate hence faces the porous spongy or cancellous bone of the head of the long bone. The cancellous bone is the porous bone underlying the so called "roman arch" of exterior, more solid bone of the articular surface e.g. of the humerus. Accordingly, after fixation of the fracture, the first side of the supportive plate typically is oriented centromedullarly, whereas the second side is oriented to the articular surface (see e.g. FIG. 3 a-c).

The sides of the articular supportive plate may have a smooth or rough surface texture. In particular embodiments, the two sides of the articular supportive plate may have a different surface texture. In preferred embodiments, the articular supportive plate is substantially planar, but can optionally have an upstanding lip at one side.

The optimal size and surface area of the articular supportive plate may depend on the patient and the type of long bone and fracture. Accordingly, the articular supportive plate may be available in various sizes and shapes. In particular embodiments, the size of the articular supportive plate ranges between 2 and 5 cm, more particularly between 2 and 3 cm. In particular embodiments, the size of the articular supportive plate is adaptable. For example, the articular supportive plate may be cuttable or breakable. More particularly, the articular supportive plate may comprise a cuttable meshed structure or lattice structure (see further).

For proximal humeral fractures, the size and surface area of the articular supportive plate is typically proportional to the size and surface area of the (anatomical) neck of the humerus, thereby allowing sufficient contact between the articular supportive plate and the caput humeri. Preferably, the size is slightly smaller, for example up to 10, 20, 30 or 40% smaller than the size of the anatomical neck of the humerus, such that the articular supportive plate does not protrude (or protrudes minimally) from the bone.

For the other fractures envisaged herein, the dimensions of the supportive plate will correspond to the dimensions of the other articular surfaces of the head of the long bones in a similar way as described for the humeral fractures, i.e. they will be slightly smaller, for example up to 10, 20, 30 or 40% smaller than the size of the inner diameter of the articular surface, such that the articular supportive plate does not protrude (or protrudes minimally) from the bone. In particular embodiments, the size of the articular supportive plate ranges between 2 and 5 cm, more particularly between 2 and 3 cm. In particular embodiments, the size of the articular supportive plate is adaptable as explained herein.

In certain embodiments, the shape of the articular supportive plate is circular, oval, polygonal, star-shaped, or cruciform. In particular embodiments, the shape is circular, oval, or polygonal.

The thickness of the articular supportive plate is typically such that the articular supportive plate has a sufficient stiffness and allows securing one or more pins or screws, while keeping the volume relatively low. In particular embodiments, the thickness of the articular supportive plate ranges between 1 and 5 mm.

The articular supportive plate described herein and the one or more fin(s attached thereto comprise one or more pin receiving features for receiving a pin or a screw, more particularly a pin or a screw of a diaphyseal plate or containment plate (see further).

Figure 4A:
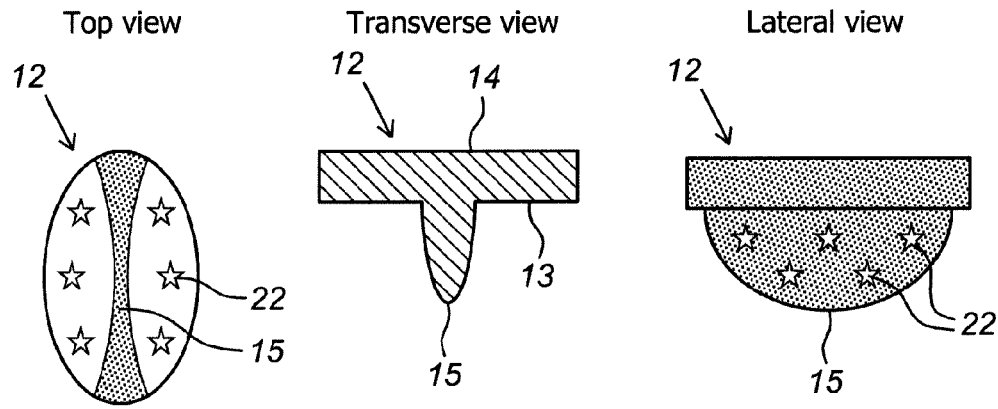
FIG. 4: Schematic view of the articular supportive plate (12) of the present invention, indicating a plate with a first side (13) and a second side (14), said first side (13) holding one (a) or more (b) fins (15). The number, shape and positioning of the screw or pin receiving features (22), for example through holes (22) or protruding fingers (30), in or on the plate are not to be seen as limiting the scope of protection of the articular supportive plate in any way. (c): Positioning of upstanding tab or lip (23) to prevent slipping of the humeral head (2) in case of varus fracture. (d): Lateral view of a supportive plate (12) and fin (15) with a honeycomb structure (left) or with protruding fingers (right) able to receive screws from a variable angle resulting in a stable construct. (e): detailed projection of possible embodiment of the supportive plate and fin, both equipped with protruding fingers (30), which function as a locking means for attaching the fin(s) (15) to the first side (13) of the articular supportive plate (12) in the desired position and orientation, and (f): at the same time, said fingers enable the angle-stable reception of screws (20' and (20"), in both the surface (first side) of the supportive plate (12) and the fin(s) (15).
Figure 4B:
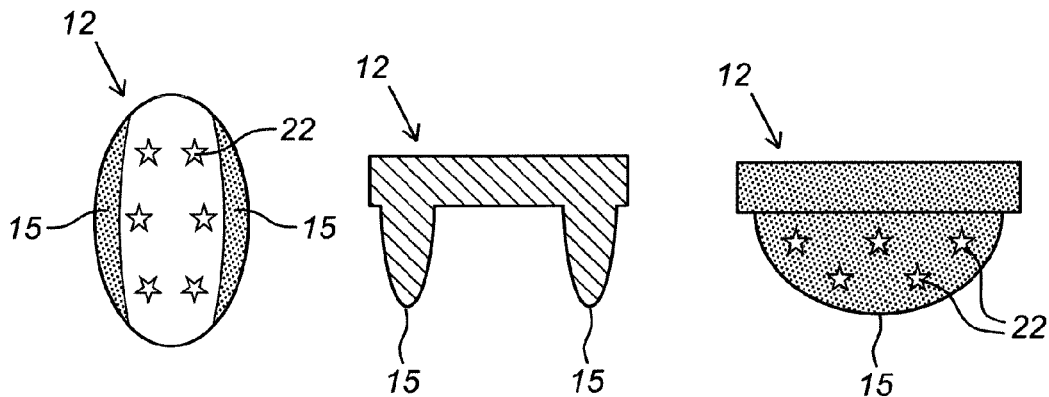
Figure 4C:
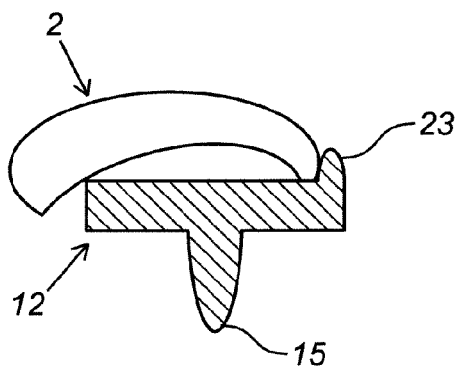
Figure 4D:
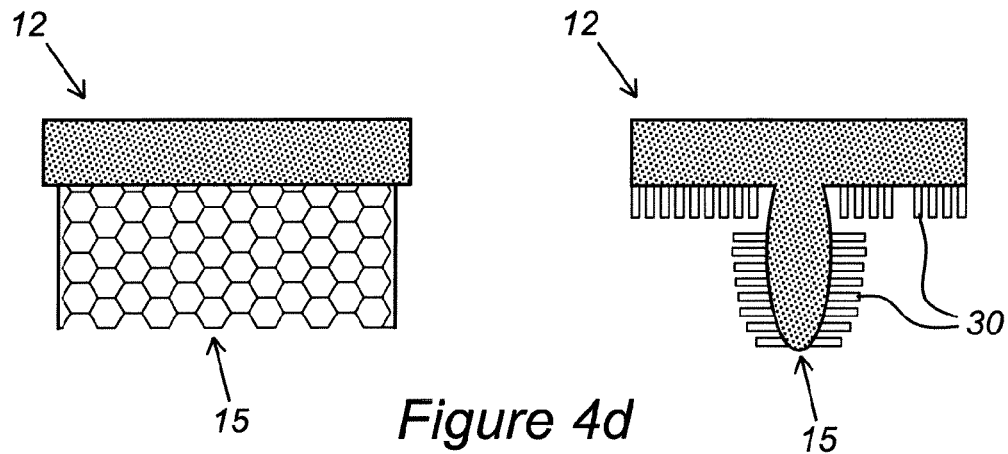
Figure 4E:
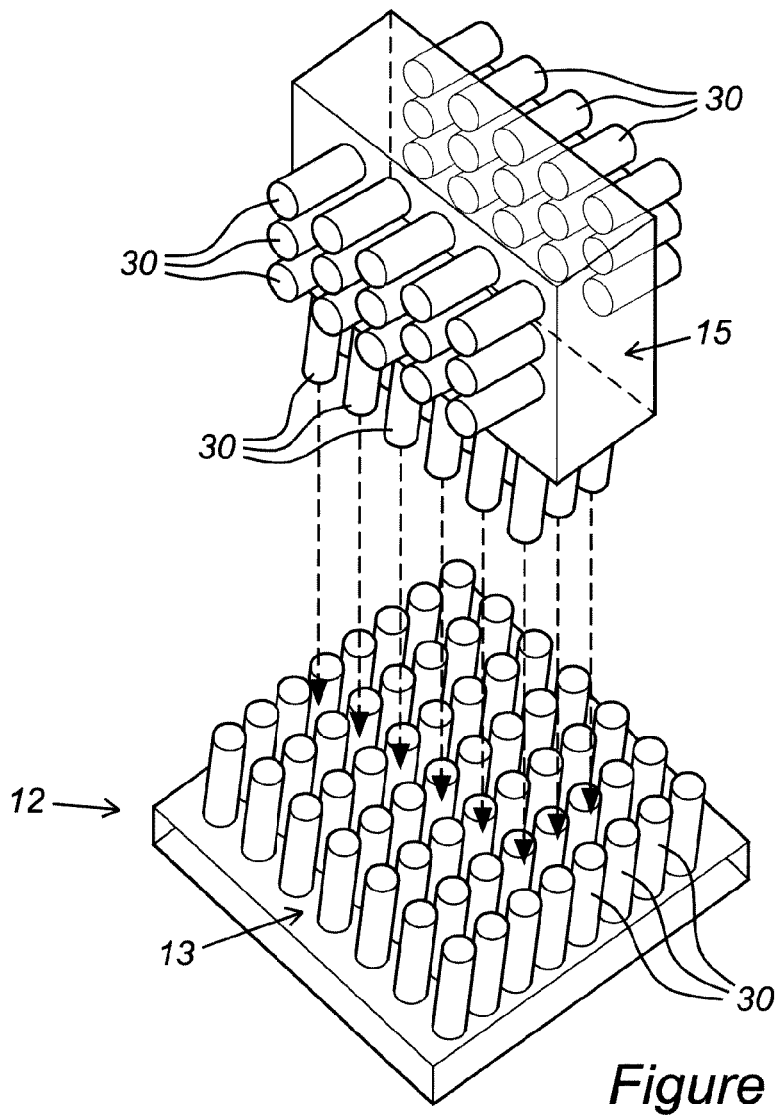
Figure 4F:
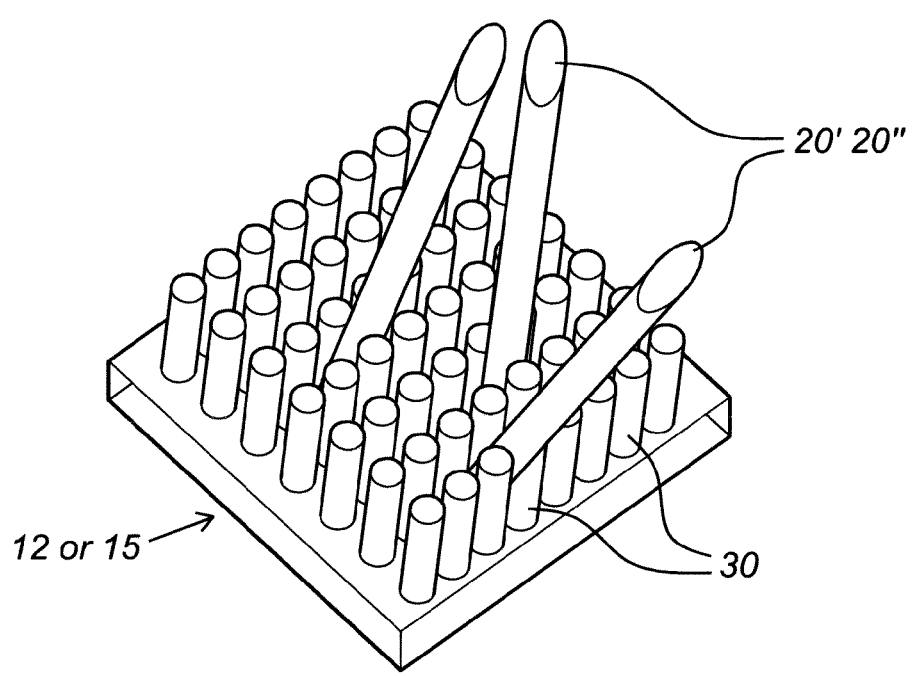
Figure 5A:
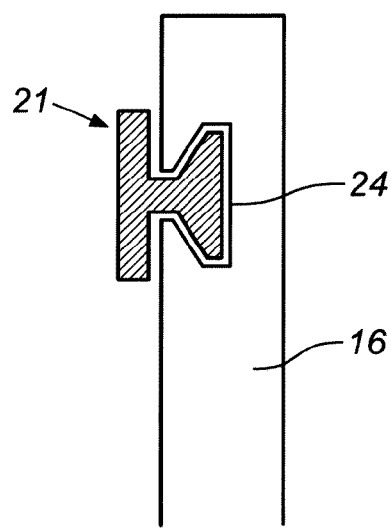
FIG. 5: Schematic view of a possible flexible attachment system of the containment plate (21) to the diaphyseal plate (16). (a): Adjustable way of sliding the containment plate, through the use of an adjustable or pivoting attachment means (26) onto the diaphyseal plate via a rail (24). (b): Positioning of the through holes (25) and the tunnel rails (24) for positioning the containment plate onto the diaphyseal plate. (c): Exemplary assembly of the containment plates (21) unto the diaphyseal plate (16) allowing adjustment of the containment plate onto the humeral head for maximum support. (d): Positioning of a typical kit according to the present invention onto the humeral head (2). Said kit in this case comprises an articular supportive plate, a diaphyseal plate, a set of diaphyseal screws and metaphyseal screws or pins that are preferably adjustable in length, and one or more containment strip(s)
Figure 5B:
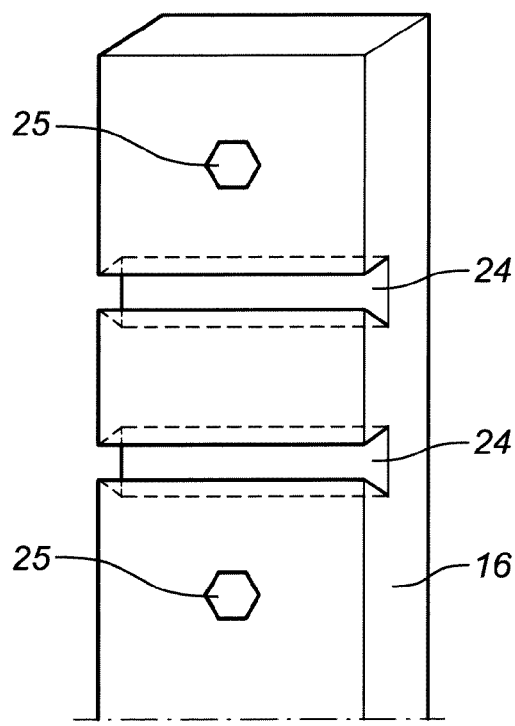
Figure 5C:
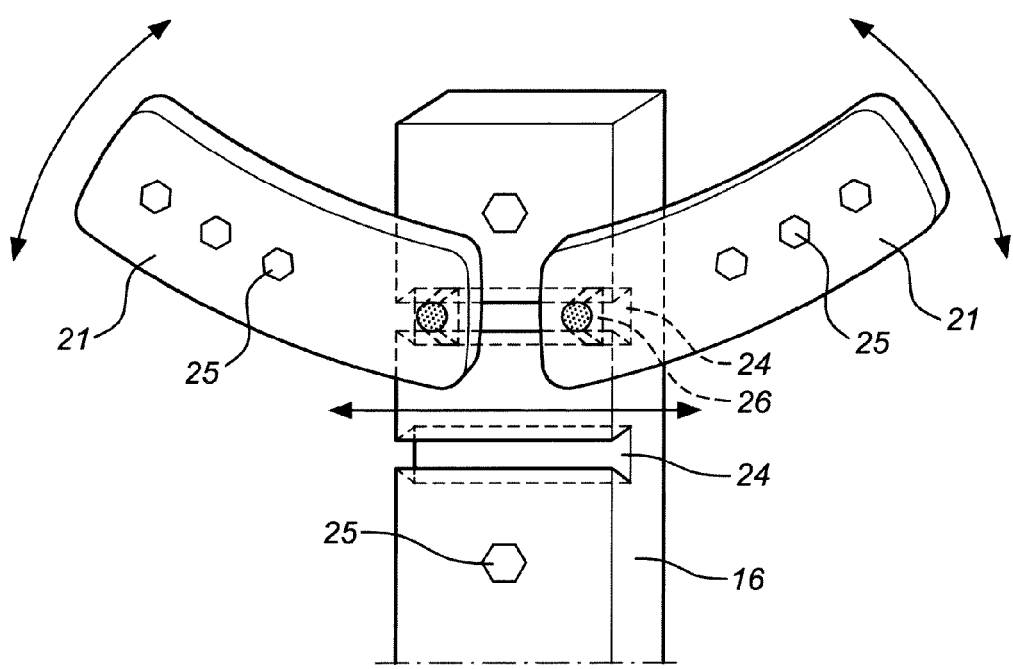
Figure 5D:
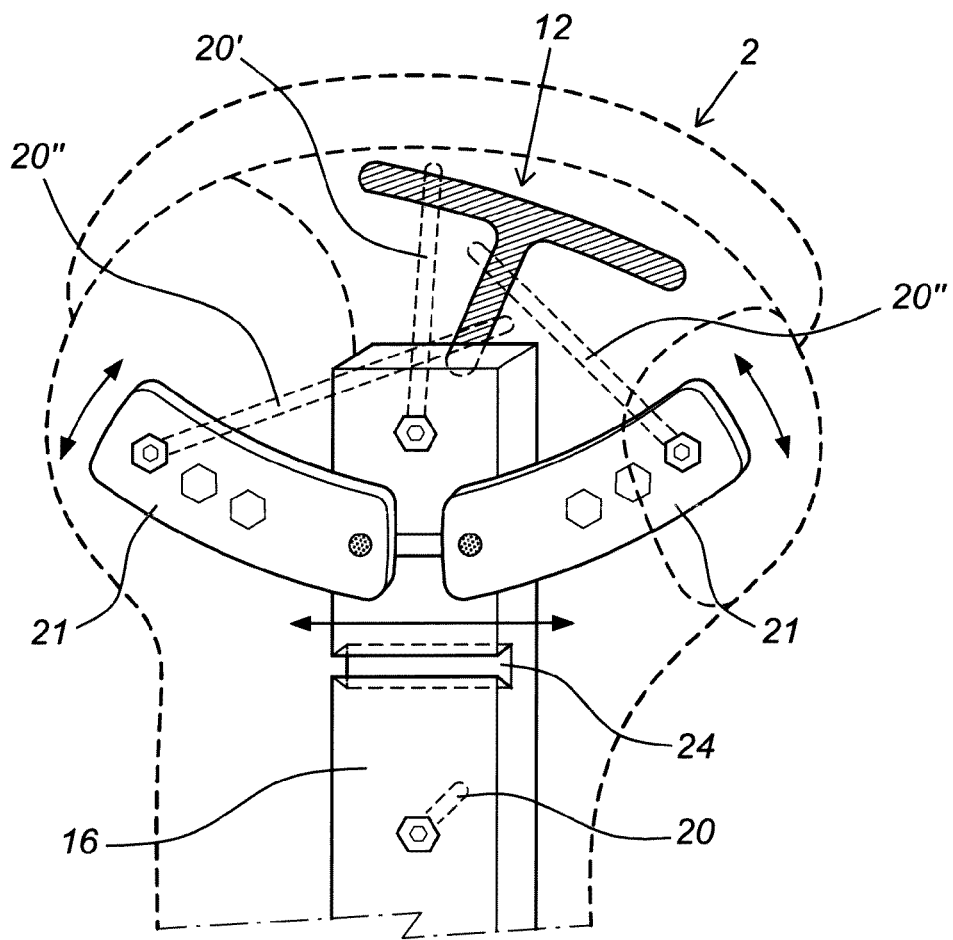

In particular embodiments, the pin receiving features may comprise a brush or array of upstanding "rods", also referred herein as studs", or "fingers" (30), protruding from the first side (13) of the supportive plate (12) (see FIGS. 4d, e and f). In particular embodiments, the brush of fingers is comparable to the fingers provided on individual blocks of Stickle Bricks™ of Hasbro Inc., but with dimensions that correspond to the dimensions of the articular supportive plate envisaged herein. The inventors have found that such systems are surprisingly suitable for receiving and holding pins and/or screws (20', 20") in a wide range of angles (see FIG. 4f). Moreover, these systems may further provide a coupling mechanism for coupling one or more fins (15) to the supportive plate (12) (see FIG. 4e). Any other similar screw receiving feature is of course also envisaged herewith.

Accordingly, in particular embodiments, the pin receiving features may comprise a plurality of fingers provided on the first side of the supportive plate, more particularly positioned substantially perpendicular to the surface of the supportive plate or of the fin(s). In further embodiments, the plurality of fingers form one or more arrays. The term "array" as used herein refers to a 2D array, i.e. an arrangement in rows and columns. The individual rows, and/or the individual columns of the array may have an equal or unequal length. In certain embodiments, the array is a rectangular arrangement in rows and columns.

Typically, the distance between adjacent fingers in a row is identical through the entire array. Similarly, the distance between adjacent fingers in a column may be identical through the entire array. In certain embodiments, the distance between adjacent rows and columns is identical through the entire array.

In certain embodiments, the array comprises a rows and b columns, wherein a and b are integers greater than 1, wherein the total number of fingers in the array is greater than 7. In further embodiments, a and b are integers greater than 2, wherein the total number of fingers in the array) is greater than 14, preferably greater than 15, more preferably greater than 24.

The fingers typically are elongated structures, having an aspect ratio of at least 2, preferably at least 3, most preferably at least 4. In preferred embodiments, the fingers have a cylindrical shape.

Typically, the optimal distance between adjacent fingers in a row or column of the array will depend on the diameter of the pins and/or screws envisaged for use during surgery. More particularly, in order to accommodate a pin or screw, the gap between adjacent fingers is preferably slightly smaller, e.g. about 2 to 20% smaller than the diameter of the pin or screw. Indeed, the fingers are typically slightly flexible, such that the array can accommodate structures having sizes which are slightly larger than the gap between the fingers. On the other hand, the fingers preferably still have a sufficient stiffness to allow for a tight fit of the screw in the array.

In particular embodiments, the gap (i.e. distance from edge to edge) between two adjacent rods, studs or fingers in a row or column throughout the array is between 0.2 and 5 mm, more particularly between 0.5 and 4 mm, most particularly between 0.5 and 2 mm.

The diameter of the rods, studs or fingers in the array typically are of a similar size of the gap between adjacent fingers. This is particularly advantageous when the arrays of fingers will also be used as coupling features (see further).

In particular embodiments, the articular supportive plate comprises one or more pin receiving features which are holes. The holes may be through holes or blind holes, preferably threaded. In particular embodiments, at least one pin receiving feature provided on the supportive plate is a through hole (from the first side to the second side of the articular supportive plate). In preferred embodiments, the articular supportive plate comprises at least two, three, four, five, or more through holes for receiving a pin or a screw.

In addition to one or more holes for receiving a pin or a screw, the articular supportive plate may further comprise one or more through holes for allowing the passage of blood and growing bone cells through the articular supportive plate. In certain embodiments, the articular supportive plate may have a meshed or porous structure.

More particularly, the articular supportive plate may comprise at least one lattice structure, i.e. a structure which consists of an open framework, for example made of strips, bars, girders, beams or the like, which are contacting, crossing or overlapping in a regular pattern. The strips, bars, girders, beams or the like may have a straight shape, but may also have a curved shape. Thus, the lattice structure is typically a framework which contains a regular, repeating pattern, wherein the pattern can be defined by a certain unit cell. A unit cell is the simplest repeat unit of the pattern. Various unit cell shapes are envisaged, including but not limited to hexagonal (resulting in a honeycomb-like structure, see e.g. FIG. 4d), and square (resulting in a checkerboard pattern).

Preferably, the lattice structure is a two-dimensional (2D) lattice structure, i.e. wherein the unit cell is repeated in only two directions. Accordingly, the lattice structure may be considered as a reticulated structure having the form and/or appearance of a net or grid. However, it is envisaged that in particular embodiments, the lattice structure is a three-dimensional (3D) lattice structure, i.e. wherein the unit cell is repeated in three directions.

In preferred embodiments, the lattice structure provides openings for receiving a pin or a screw. More particularly, each unit cell may provide an opening for receiving a pin or a screw. The size of the openings typically depends on the distance between the strips and the like in the lattice structure. In particular embodiments, the opening size of the lattice structure is between 0.2 and 5 mm, more particularly between 0.5 and 4 mm, most particularly between 0.5 and 2 mm.

The strips, bars, girders, beams or the like preferably have a thickness or diameter of 1 mm or more. This may enable sufficient mechanical strength to the articular supportive plate, while still allowing the girders to be cut, for example to adapt the size of the articular supportive plate to the size of the caput humeri. In particular embodiments, the strips, bars, girders, beams or the like preferably have a thickness or diameter of 1.0 mm, 1.5 mm, 3 mm, 4 mm, 5 mm or more.

It is also envisaged that in certain embodiments the articular supportive plate may have a solid, non-meshed structure.

In particular embodiments, the articular supportive plate described herein may comprise one or more fins, which are projecting from the first side of the articular supportive plate, opposite to the side of the articular supportive plate interacting with the caput humeri. More particularly, the fins are arranged such that, after fixation of the bone, they have a centromedullar orientation (see FIG. 3 a-c).

The fin(s) typically form a (narrow) standing ridge. The height of the fin(s) may be uniform or non-uniform. For example, one or more fins may have an arcuate shape. In particular embodiments, the maximal height of the fin(s) ranges between 0.75 and 3 cm. The thickness of the fin may be uniform or non-uniform. In certain embodiments, the thickness of the ridge ranges between 1 and 5 mm. In certain embodiments, the total length of the fin(s) ranges between 1.5 and 3 cm. In particular embodiments, the fin(s) are planar.

However, it is also envisaged that the fin(s) may have a bent or curved shape. In particular embodiments, a fin may be curved to optimize the direction towards one or more particular bone parts, more particularly a tuberosity. This may facilitate receiving pins or screws for fixation of said bone parts.

The fin(s) typically are fixed to the articular supportive plate such that the relative position of the articular supportive plate and the fin(s) is locked. In particular embodiments, the articular supportive plate and the fin(s) form a single part.

However, it is also envisaged that in particular embodiments, the fin(s) are provided as separate elements, which can be (removably) fixed to the articular supportive plate. Accordingly, the fins may be attached, or at least attachable to the articular supportive plate. Indeed, the fin(s) and the articular supportive plate may both be provided with one or more coupling features allowing coupling of the fin(s) to the articular supportive plate. Preferably, the coupling features allow for a reversible coupling of the fin(s) to the articular supportive plate. Various types of coupling features are envisaged. In particular embodiments, the coupling features comprise elements or combinations of elements selected from the group consisting of interlocking features, a snap-fit system, a dovetail system, and a pinned system.

In particular embodiments, the articular supportive plate and the fin(s) are provided with interlocking spatial components, i.e. a plurality of interlocking coupling features, for example 2, 3, 5, 10, 15, 20, 50 or more coupling features.

This may provide alternative possibilities of coupling the fin(s) to the articular supportive plate, such that the osteosynthesis device can be assembled according to the specific nature of the fracture. In preferred embodiments, the coupling features are arranged in a regular pattern. In certain embodiments, the articular supportive plate and fin(s) are both provided with a multitude of coupling features, for example 2, 3, 5, 10, 15, 20 or more coupling features. In such embodiments, coupling of a fin to the articular supportive plate is typically obtained via an interaction of two or more pairs of said coupling features. As a non-limiting example, the coupling features may include rods, studs or fingers, such that the fin(s) and support structure may be in the manner of Lego™ blocks or Stickle Bricks™.

Indeed, in certain embodiments, the supportive plate and the fin(s) both comprise a plurality of coupling features, said coupling features forming an array of studs or fingers as described above. This may allow for reversible coupling of the fin(s) to the supportive plate through interlocking of the fingers provided on the fin(s) with the fingers provided on the supportive plate, in the manner of coupling Stickle Bricks™ (see FIG. 4e).

In certain embodiments, the supportive plate may be provided with an array of fingers or studs protruding from the first side of the supportive plate, and the fin(s) may be provided with an array of receptacles sized to snugly receive the fingers or studs. The studs and receptacles may provide a similar coupling mechanism as the studs and receptacles provided on LEGO® blocks. In alternative embodiments, the fingers or studs may be provided on the fin(s) and the receptacles may be provided on the supportive plate. In certain embodiments, the receptacles may be provided as through or blind holes. In certain embodiments, these holes may also be used as pin receiving features.

In particular embodiments, combinations of various coupling features as described above may be provided on the supportive plate and/or fin(s).

Both the surface of the first side (13) of the supportive (articulate) plate and the fin(s) (15) can have screw or pin receiving means as defined herein (30). This enables receiving screws or pins from various directions, e.g. coming from the diaphyseal bone plate or from the containment strips (cf. FIG. 4e). More particularly, the pin receiving means of the supportive plate may allow for receiving pins or screws from a direction which is different from the direction of the pins or screws received by the pin receiving means of the fin(s).

If the articular supportive plate has a meshed structure or lattice structure as described above, it is envisaged that the coupling features of the fin(s) may allow coupling of the fin(s) to the articular supportive plate via the holes provided by the meshed structure or lattice structure of the articular supportive plate.

Each of said one or more fin(s) is provided with pin receiving features for receiving a pin or a screw. In preferred embodiments, each fin is provided with two, three, four, five, ten, or more pin receiving features. More particularly, the pin receiving features can allow for receiving a pin running in a direction not parallel to the fin surface, for example under an angle between 5° and 90°, more particularly an angle of at least 10°, 20°, 30°, 40°, 50°, 60°, or more. This helps to ensures that the supportive plate and fin(s) can receive pins and/or screws from various directions.

In particular embodiments, the pin receiving features form a brush or array of fingers as described above. In certain embodiments, the pin receiving features may comprise one or more through holes or blind hole. In further embodiments, the pin receiving features may comprise one or more threaded holes, preferably threaded through holes.

The pin receiving features may allow for fixation of the fracture, together with a diaphyseal plate and optionally one or more containment strips (e.g. containment plates, see further). In preferred embodiments, each fin is provided with at least two, three, four, five, or more through holes for receiving a pin or a screw. In particular embodiments, the fin(s) may comprise a meshed structure as described above. The holes provided by the meshed structure may allow for a maximized screw or pin acceptance. In further embodiments, the fin(s) and articular supportive plate both comprise a meshed structure. The unit cells of the meshed structure of the fin(s) and the articular supportive plate may differ or be identical.

In particular embodiments, the fin(s) are arranged perpendicularly to the articular supportive plate. The term "perpendicular" as used herein is to be understood as including a certain amount of derivation from its actual precise orientation. More particularly, a fin is considered perpendicular to the articular supportive plate if the angle between the plane best fitting the fin and the plane best fitting the articular supportive plate is between 80° and 100°, preferably between 85° and 95°, more preferably between 89° and 91°.

In particular embodiments, the articular supportive plate comprises a single fin, preferably projecting from a central part of the articular supportive plate.

In other embodiments, the articular supportive plate comprises two or more parallel fins projecting from the articular supportive plate. In preferred embodiments, two of said two or more parallel fins project from lateral parts of the articular supportive plate. The term "parallel" as used herein is to be understood as including a certain amount of derivation from its actual precise orientation. More particularly, two fins are considered parallel if the angle between the planes best fitting the fins does not exceed 10°, preferably 5°, most preferably 2°.

In particular embodiments, the articular supportive plate described herein is further provided with a lateral upstanding tab or lip, straight or bent. In preferred embodiments, said tab is provided on the second side of the articular supportive plate (opposing the side optionally comprising one or more fins). More particularly, the tab may be located on a part of the articular supportive plate which is to be positioned near the medial calcar of the humerus. The tab (23) may prevent the caput humeri (2) from sliding off the articular supportive plate (12) (see FIG. 4c), which may occur in unstable fractures. In particular embodiments, the tab is arranged perpendicular to the articular supportive plate. Preferably, the height of the tab is between 2 and 5 mm and the width between 0.5 and 1 cm.

In particular embodiments, the second side of the articular supportive plate (opposing the side optionally comprising one or more fins) may comprise one or more protrusions such as pins or the like. This may increase the stability of the articular supportive plate when mounted on the caput humeri. On the other hand, such protrusions may also impede repositioning of the articular supportive plate. Accordingly, it is envisaged that in particular embodiments, the second side of the articular supportive plate does not comprise such protrusions.

As described above, the supportive plate and/or fin(s) may be provided with a plurality of fingers, which may allow for receiving a pin or screw within a range of selectable angles. This may significantly facilitate the use of the kit described herein. However, there are also other possibilities for allowing receiving a screw within a range of angles.

Indeed, in certain embodiments, the articular supportive plate and/or fin(s) may be provided with one or more (through) hole(s) which are configured to receive a variable angle locking screw. Variable angle locking screws can be inserted in or through a screw hole and locked to the articular supportive plate at a selectable angle within a range of selectable angles. International patent application WO2009023666 (Synthes), which is hereby incorporated by reference, describes en exemplary type of variable angle locking screws and holes suitable for use in the support plat of the present invention. In said variable angle locking screws and holes, the range of selectable angles may form a cone of about 30 degrees about the central axis of the screw hole. Accordingly, the angle of the screw can vary from 0 degrees to about 15 degrees in any direction away from the central axis of the hole. The screws do not require a bushing, a compression cap, an expandable ring, or an expandable head to lock the angular position of the screw relative to the articular supportive plate.

However, it is envisaged that in particular embodiments, one or more of the (through) hole(s) provided on the articular supportive plate and/or fin(s) thereof may be provided with a bushing, a compression cap, or an expandable ring to lock the angular position of a normal (i.e. non-variable angle) screw relative to the articular supportive plate. For example, the (through) hole(s) may be provided with a threaded locking ring which is made from a material that is more deformable than the material of the diaphyseal plate. Examples of such locking rings are described in international patent application WO 2009/114094 (Orthohelix Surgical Designs Inc.), which is hereby incorporated by reference.

In particular embodiments, at least one through hole is provided on the articular supportive plate and/or fin(s) thereof, said through hole comprising a stopping feature, to ensure that the screw or pin does not proceed further through the hole after a certain length. However, it is also envisaged that a stopping feature is provided on the screws instead of the screw holes. Indeed, the screw may comprise a threaded and a non-threaded part (see further).

In particular embodiments, the articular supportive plate (and/or one or more fins provided thereon) may comprise one or more dedicated engagement features allowing for engagement of an instrument used for fracture reduction. Examples of such instruments include K-wires, elevators and osteotomes, which can be operated manually or through a robotic steering element. Exemplary engagement features may include shaped protrusions and/or holes, such as threaded holes.

In a further aspect, provided herein is a kit or articular fracture fixation system, comprising an osteosynthesis device as described herein, and further comprising a diaphyseal plate. Diaphyseal plates (also known as diaphysis plates, or osteosynthesis plates) are well-known in the art and are used for internal fixation of bones, i.e. fixing two or more bone fragments. The term "bone fragments" as used in the context of the present disclosure refers to partially or completely separated parts originating from one bone, for example a humerus, as is depicted for example in FIG. 1. Diaphyseal plates have a rigid structure such that, after fixation to the bone or bone fragments they can maintain these in position even under stress conditions, thereby allowing the bone to heal.

Diaphyseal plates typically comprise a bone-facing surface and an opposing outer surface. The diaphyseal plate comprised in the kit as described herein comprises a longitudinal distal plate portion for contacting the diaphysis of a long bone (e.g. a humerus), and a proximal plate portion to be positioned on or near the epiphysis of a long bone (e.g. the caput humeri of said humerus). The term "longitudinal" as used herein refers to objects having an aspect ratio (length divided by width) of at least 2, preferably at least 3, most preferably at least 4.

In particular embodiments, the proximal plate portion extends laterally outward from the longitudinal axis of said distal plate portion, forming an angle between 130° and 140°, preferably about 135°. This may allow the diaphyseal plate to closely follow the neck-shaft angle of e.g. the human humerus, which on average is about 135°.

The distal portion of the diaphyseal plate is provided with at least one through hole (from the bone-facing surface to the outer surface) for securing the diaphyseal plate to the diaphysis of the long bone, for example via a pin or a screw. Preferably, the distal plate portion is provided with at least two, three, four, five, or more through holes for receiving a pin or a screw.

In the diaphyseal plate provided by the kit described herein, also the proximal portion of the diaphyseal plate is provided with at least one through hole (from the bone-facing surface to the outer surface) for receiving a pin or a screw. More particularly, at least one through hole of the proximal plate portion and at least one of said pin receiving features of said articular supportive plate or fin(s) are configured to respectively send and receive the same screw or pin. Preferably, the through holes of the proximal plate portion and the pin receiving features of the articular supportive plate or fin(s) are configured to respectively send and receive the same screws or pins. This allows locking the relative position of the diaphyseal plate, the articular supportive plate, and the bone fragments between and/or near the diaphyseal plate and articular supportive plate. In particular embodiments, the at least one through hole of the proximal plate portion is configured to receive a variable angle locking screw as described herein.

In particular embodiments, at least one of the through holes provided on the diaphyseal plate comprises a stopping feature, to ensure that the screw or pin does not proceed further through the hole after a certain length. However, it is also envisaged that a stopping feature is provided on the screws instead of the screw holes.

In particular embodiments, the diaphyseal plate may be a standard commercially available diaphyseal plate, more particularly a proximal humeral locking plate. A variety of standard diaphyseal plates is, among others, provided by Synthes Holding A G, Depuy Orthopaedics, Konigsee Implante and Instrumente zur Osteosynthese GmbH, Acumed LLC, Zimmer GmbH, Biomet, Stryker Corporation, or the like. Non-limiting examples of suitable commercially available diaphyseal plates include the Biomet $S^3$™ plate, and the Synthes LCP proximal humerus plate.

In particular embodiments, the diaphyseal plate consists of a single piece comprising a proximal and distal part as described above.

In other embodiments, the proximal and distal plate portion may be provided as two separate parts, which may be (removably) coupled to each other. More particularly, the proximal and distal plate portion may each comprise a coupling feature for coupling the proximal plate portion to the distal plate portion, thereby locking the relative position of these parts. In particular embodiments, the coupling features comprise elements or combinations of elements selected from the group consisting of interlocking features, tunnels, a snap-fit system, a dovetail system, and a pinned system. Preferably, the coupling features allow for more than one possibility to couple the proximal plate portion to the distal plate portion. Accordingly, the size and/or shape of the diaphyseal plate may be adjusted to a specific bone. In particular embodiments, the coupling features provide a rail system, such that the relative position of the distal plate portion and the proximal plate portion can be variably locked.

In particular embodiments, the diaphyseal plate may comprise one or more dedicated guiding features. Such features may include holes for receiving a K-wire, wherein the K-wire may be used for determining the correct position of the diaphyseal plate on the diaphysis, or for determining the correct relative orientation of the diaphyseal plate to the articular supportive plate.

In particular embodiments, the kit may comprise two, three, four, five, or more diaphyseal plates as described herein. For example, the kit may comprise diaphyseal plates of various sizes. Additionally or alternatively, the kit may comprise a diaphysial plate wherein the size and/or shape may be adjusted, as described above.

In certain embodiments, the kit may comprise two, three, four, five, or more articular supportive plates as described herein. For example, the kit may comprise articular supportive plates of various sizes and/or shapes. However, it is also envisaged that the kit may comprise an articular supportive plate wherein size of the articular supportive plate is adaptable, as described herein.

In particular embodiments, the kit described herein further comprises at least one containment strip or band (also referred to herein as containment plate or strip). The containment strip may provide additional stabilization of comminuted and/or multiple fractures. In particular embodiments, the containment strip may be used for fixation of one or more of the bulbous structures on the head of the long bone, such as the tuberosities, tubercles, malleoli, condyles, styloid processes or the like, for example the greater tuberosity and/or the lesser tuberosity of the humerus.

In particular embodiments, the containment strip typically has a width between 0.4 and 1.5 cm, for example about 8 mm. The length of the containment strip may depend on the type of bone and fracture. In certain embodiments, the length may be between 1 and 4 cm. The thickness of the containment strip typically is between 0.5 and 5 mm, for example about 1 mm. Typically, the thickness is chosen such that the containment strip is malleable or flexible (see further).

The shape of the containment strip is preferably such that it allows contacting and at least partially surrounding at least one bulbous structure, preferably including at least said bulbous structure. In particular embodiments, the containment strip may have a branched structure, and/or provide a basket-like structure. The optimal shape of the containment strip may depend on the patient and the type of fracture. In particular embodiments, the containment strip is flexible or malleable. This allows for adapting the shape of the containment strip to the shape of e.g. the caput humeri. The term "flexible" as used herein means capable of being bent or flexed (without breaking) by forces typically produced by manual manipulation of a human user. The term "malleable" as used herein means being capable of being permanently shaped, bent, or otherwise deformed (without breaking) by forces typically produced by manual manipulation of a human user so that the object or material referred to retains the desired deformation.

The containment strip is configured such that it can be (removably) coupled to the diaphyseal plate of the kit. More particularly, the proximal plate portion of the diaphyseal plate and the containment strip can each comprise a coupling feature for coupling the containment strip to the proximal plate portion (cf. for example FIG. 5). Preferably, the coupling features allow for locking the relative position of the containment strip and the diaphyseal plate. Different types of coupling features are envisaged. In particular embodiments, the coupling features comprise elements or combinations of elements selected from the group consisting of interlocking features, tunnels, a snap-fit system, a dovetail system, and a pinned system.

In particular embodiments, the coupling features provide a rail system (24, 26), such that the relative position of the containment strip (21) and the diaphyseal plate (16) can be variably locked (see FIG. 5). More particularly, the proximal plate portion may comprise a slit or ridge as a coupling feature, wherein the containment strip comprises a coupling feature fitting into said slit or onto said ridge.

The containment strip is further provided with one or more through holes, for receiving a pin or a screw. This allows for securing the containment strip onto the articular surface of the head of the long bone, e.g. the humerus head, more particularly onto a bulbous structure thereof, e.g. a tuberosity of the humerus. In particular, the pins or screws used for attaching the containment strip to e.g. the tuberosity can extend to the articular supportive plate of the invention (e.g. to one of the extended fins), thereby securing the attachment of said tuberosity to the humerus head (cf. e.g. FIG. 3*a*).

In particular embodiments, the kit comprises two or more containment strips as described above, which may be coupled simultaneously to the diaphyseal plate. In a further example, a first containment strip may be used for fixation of the lesser tuberosity, whereas a second containment strip may be used for fixation of the greater tuberosity of the humerus.

In particular embodiments, the surface of the articular supportive plate, diaphyseal plate, containment strip, pins and/or screws may comprise one or more markers, which may help the surgeon in performing the fixation. Possible markers include, but are not limited to letters, numbers, symbols, specific colors, shapes, and the like.

The materials used in the articular supportive plate, diaphyseal plate and optional containment strip of the kit as described herein typically are materials which are compatible with the human or animal body. Preferably, these materials should ensure the mechanical stability of the articular supportive plate, diaphyseal plate and optional containment strip for at least 6 to 8 weeks.

In particular embodiments, the articular supportive plate and diaphyseal plate are independently formed of one or more materials selected from the group consisting of titanium, titanium alloy, stainless steel, cobalt-chromium alloy, tantalum, tantalum alloy, polyethylene, polyether ether ketone (PEEK), a polyanhydride, a poly(ethylene glycol)-based material (such as poly(ethylene glycol)-diacrylate or poly(ethylene glycol)-dimethacrylate) and bioceramics. These materials are biocompatible and may provide the strength and durability required for implants. Bioceramics are ceramics that are compatible to the human body, such as calcium phosphate ceramic.

In certain embodiments, the surface of the articular supportive plate and/or diaphyseal plate may comprise a porous metal, preferably porous tantalum, more preferably Trabecular Metal™ (available from Zimmer). Porous metal such as Trabecular Metal™ closely resembles the physical and mechanical properties of bone more and may therefore enable rapid and extensive tissue infiltration and strong attachment.

In particular embodiments, the articular supportive plate, diaphyseal plate and/or optional containment strip may comprise one or more biodegradable materials. An overview of various materials used for manufacturing biodegradable orthopedic implants is provided by Park et al. (Park H, Temenoff J S, Mikos A G. Biodegradable orthopedic implants. In: Bronner F, Farach-Carson M C, Mikos A G, eds. Engineering of Functional Skeletal Tissues. Springer, 2007: 55-68). In particular embodiments, the biodegradable materials may comprise materials selected from the list consisting of poly(lactic acid), poly(D-lactic acid), poly (L-lactic acid), poly(glycolic acid), poly(ε-caprolactone), poly(dioxanone), poly(lactide-co-glycolide), poly(propylene fumarate) (PPF), oligo(poly(ethylene glycol) fumarate), poly(glycolide-co-trimethylene carbonate), a polyorthoester, and a polyanhydride.

In particular embodiments, the articular supportive plate and/or diaphyseal plate may comprise a hydroxyapatite coating. The use of a hydroxyapatite coating may further improve the biocompatibility of these kit components. The hydroxyapatite coating may be provided over a part or over the entire surface of the diaphyseal plate and/or articular supportive plate.

In particular embodiments, the kit described herein may further comprise one or more pins or screws which are compatible with pin receiving features provided on the articular supportive plate and the fin(s), and with the through holes for receiving pins or screws provided on the diaphyseal plate and/or containment strip(s). In further embodiments, the kit may comprise one or more variable-angle screws as described above.

Typically, the amount and type of pins or screws required for proximal humeral fracture fixation depends on the patient and the type of fracture. Accordingly, the pins and/or screws provided in the kit may have various lengths, wherein the surgeon can choose the pin or screw having the most appropriate length.

In particular embodiments, the kit may comprise at least one screw which has an adaptable length. Such a screw is also referred to herein as "adaptable screw". This reduces the amount of screws needed in the kit, as one adaptable screw can be provided instead of a number of screws with varying lengths. In particular embodiments, the adaptable screw is cuttable or breakable, preferably using surgical (cutting) instruments.

In particular embodiments, the adaptable screw is provided with one or more weakened spots such as notches. Typically, the weakened spots facilitate cutting or breaking of the screw, while still providing the strength required for fixation and stabilization of the fracture.

In certain embodiments, the adaptable screw comprises one or more segments which are coupled linearly to each other via coupling features, such as a snap-fit system or a threaded system. Typically, the segments are provided at the end of the screw which is not entered into the bone. In such embodiments, the length of the screw may be reduced by removing one or more segments from the screw. It may further be possible to increase the length of the screw by adding one or more segments to the screw.

In particular embodiments, the adaptable screw is formed of one or more biocompatible polymers, such as polyethylene, PEEK, or mixtures or copolymers thereof. Screws manufactured from these materials may provide the strength required for fixation and stabilization of the fracture, but are typically easier to cut than screws made of metals, such as stainless steel or titanium. In certain embodiments, the adaptable screw may comprise one or more biodegradable materials.

Said adaptable screws may be secured in the diaphyseal plate or containment strip, using any kind of locking device, attachable to the cuttable or breakable end of the screw or pin.

Figure 6A:
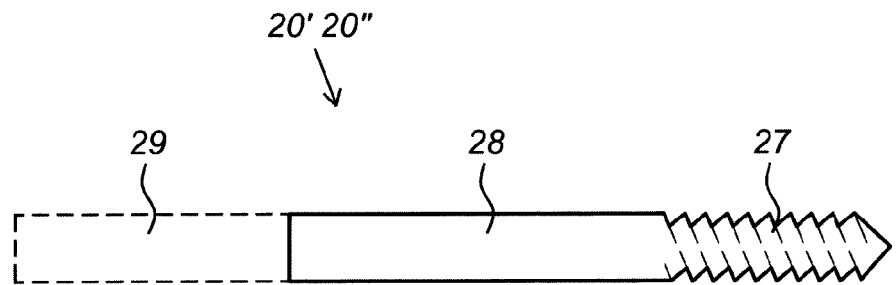
FIG. 6: Schematic view of particular embodiments of an adaptable screw as described herein. (a): Adaptable screw (20, 20', 20") having a threaded end (27), a non-threaded region (28) acting as stopping feature, and an adaptable region (29). (b): frontal view (left) and lateral view (right) of the end of an adaptable (breakable) screw (20'), engaged in a through hole of a diaphyseal plate (16).
Figure 6B:
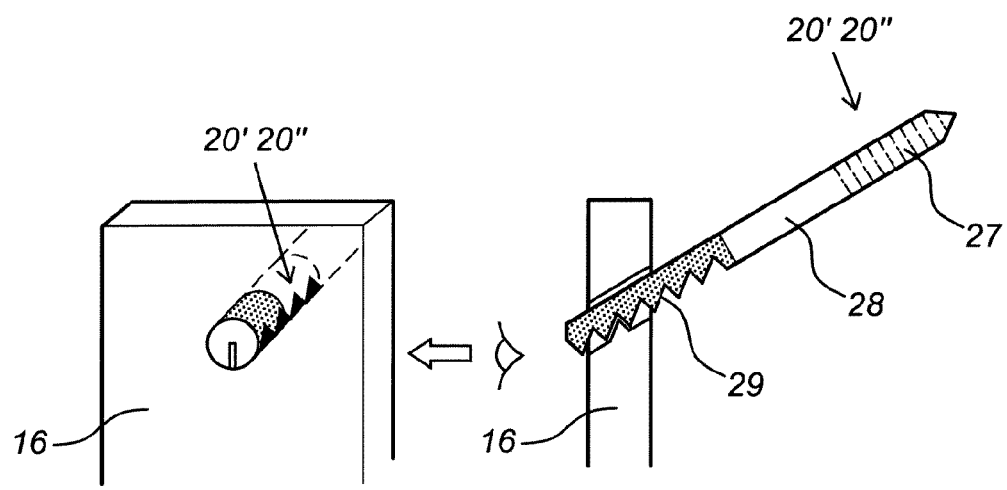

In particular embodiments, the adaptable screw (20' 20") comprises a threaded end (27), which, along the length of the screw, is followed by a non-threaded region (28) and an adaptable region (29), respectively, wherein the adaptable region forms the other end of the screw (see FIG. 6a). The threaded end may facilitate entering of the screw into the bone, whereas the non-threaded region may prevent the screw from penetrating too far into the supportive plate. The threaded end and the non-threaded region may, but need not, be adaptable.

In particular embodiments, the adaptable screw is a variable-angle screw.

In a further aspect, provided herein is a method of fixating an articular fracture in a long bone using the kit described herein. The method comprises the steps of:

(a) mounting of an articular supportive plate of the kit under the articular surface of the proximal or distal end of the long bone;
(b) securing a diaphyseal plate of the kit to the diaphysis of the long bone;
(c) reducing the fracture;
(d) locking the relative position of the articular supportive plate and said diaphyseal plate via one or more screws or pins; and
(e) optionally, coupling one or more containment strips onto the diaphyseal plate, and securing the one or more containment strips onto one or more bulbous structures of said distal or proximal end of the long bone.

Typically, the procedure is planned based on data obtained via medical imaging techniques, such as x-ray radiography. For performing the proximal humeral fracture fixation, the patient is preferably placed in a beach-chair position. The procedure may be performed using a deltopectoral approach.

The following procedure is exemplified for a proximal humerus fracture, but can be extrapolated to any one of the other fractures mutatis mutandis.

Figure 2A:
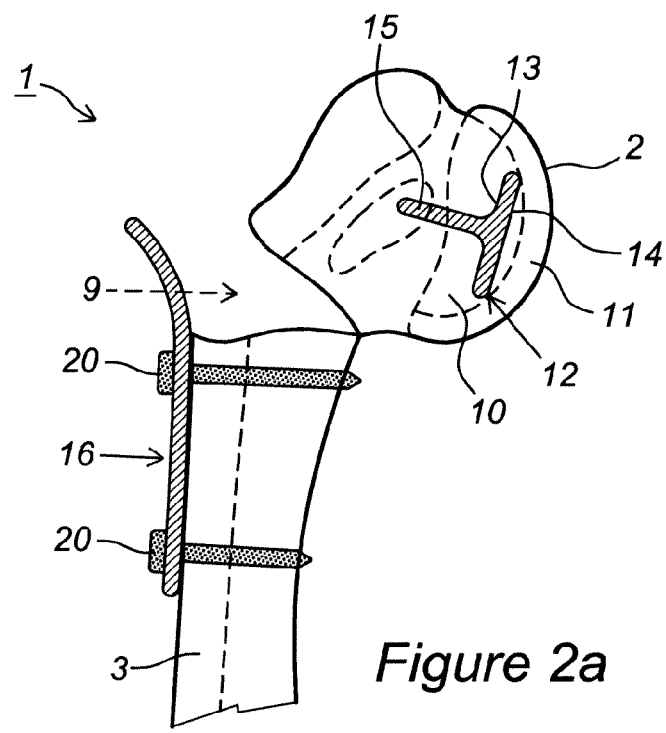
FIG. 2: Schematic view of the use of the articular supportive plate (12) of the present invention: (a): positioning of the articular supportive plate (12), having a first (13) and a second (14) side in the cancellous or porous bone (10), supporting the articular surface (11) of the caput humeri (2), wherein the one or more fin(s) (15) are oriented towards the centromedullar region of the long bone. Note that at this stage also the distal end of a diaphyseal plate (16) can (provisionally) be fixed to the diaphysis (3), using diaphyseal screws or pins (20); (b): the articular supportive plate (12) is used to reduce the fracture without damaging the bone further, note that at this stage also the distal end of a diaphyseal plate (16) can (provisionally) be fixed to the diaphysis (3), using diaphyseal screws or pins (20); (c): the reduction is almost complete, using joy-stick-like tools, linked to the articular supportive plate; (d): the fracture is correctly reduced and the proximal part of the diaphyseal plate (16) can now be secured to the humeral head, through metaphyseal screws (20') or pins, which are received by the articular supportive plate (12). The metaphyseal screws or pins (20') are received by the support plate (12) by screw receiving means (22), which can be holes or protruding finger-like structures, both enabling the stable variable angle reception of said screws or pins as discussed further.

In step (a) of the present method, an articular supportive plate (12) comprised by the kit is positioned under the articular surface of the caput humeri (2) (see FIG. 2a). In this way, the articular supportive plate may support the subchondral bone. In particular embodiments, the tuberosities may be slightly retracted to afford access under the articular surface of the caput humeri. In certain embodiments, the tuberosities may be identified and tagged, for example with sutures. The articular supportive plate may be chosen such that an optimal coverage of the articular surface is provided. The articular supportive plate is typically pressed onto or into the cancellous bone under the articular surface, but is not locked onto the bone at this stage of the procedure. Typically, the articular supportive plate will be mounted under the caput humeri in a central position. Until the relative position of the diaphyseal plate and articular supportive plate is locked in step (d), the position of the articular supportive plate may be changed if considered necessary.

Figure 2B:
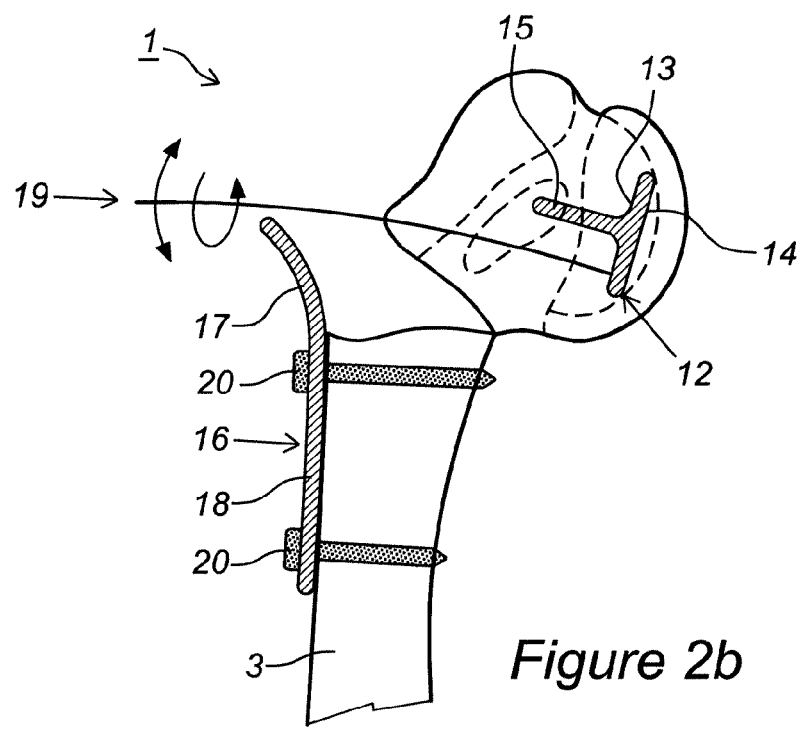

In step (b) of the present method, the diaphyseal plate (16) comprised by the kit is secured to the diaphysis (3) of the humerus (1) (see FIGS. 2a and 2b). This typically involves mounting of the diaphyseal plate (16) onto the diaphysis (3) via the bone contacting surface provided on the distal plate portion (18), while ensuring that the proximal plate portion (17) is positioned on or near (the target location of) the humeral head of said humerus. The diaphyseal plate can then be secured or locked onto the bone via one or more (optionally provisional) pins or screws (20), which are inserted into the diaphysis via the one or more screw holes provided on the distal plate portion. In particular embodiments, the diaphyseal plate is screwed onto the diaphysis of the humerus, preferably using two or more screws.

Typically, step (a) will be performed prior to step (b). However, in certain embodiments, step (b) may be performed prior to step (a).

Figure 2C:
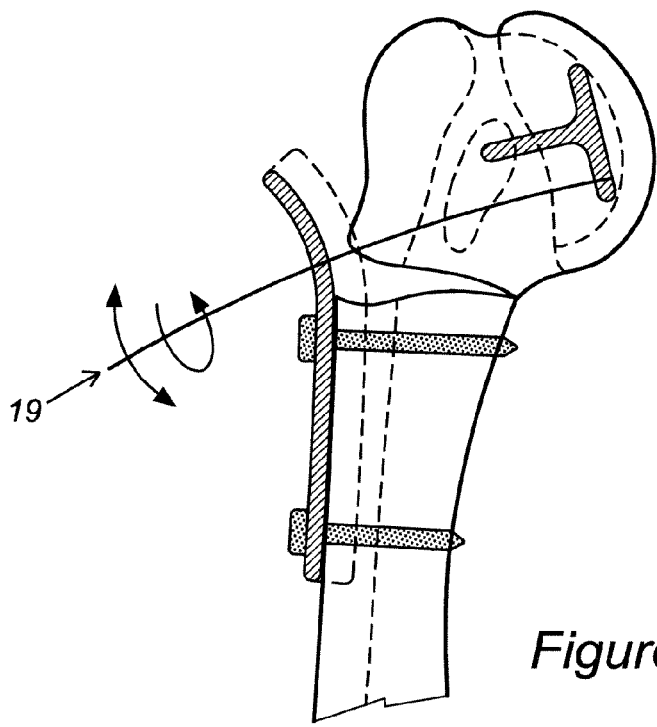

In step (c), the fracture is reduced. This may be done once the articular supportive plate is mounted onto the caput humeri. Accordingly, step (a) is typically performed before step (c). In the prior art, reduction is typically achieved using closed manipulation and instruments such as K-wires, elevators or osteotomes, as 'joystick' to move the caput humeri into position, often guided by fluoroscopy. However, the direct engagement of the reduction instruments on the bone often causes damage to the bone. Advantageously, in the methods described herein, the instruments (19) used for the reduction may act on the articular supportive plate (12) instead of directly acting on the bone, thereby avoiding further damage to the bone (see FIGS. 2b and 2c). The instruments may engage to dedicated engagement features provided on or attachable to the articular supportive plate (or fin), or any other feature such as a through hole. Compared to direct engagement of the reduction instruments on the bone, reduction of the fracture via the articular supportive plate may significantly reduce the risk of damaging the bone, and may facilitate the manipulation of the bone.

Figure 2D:
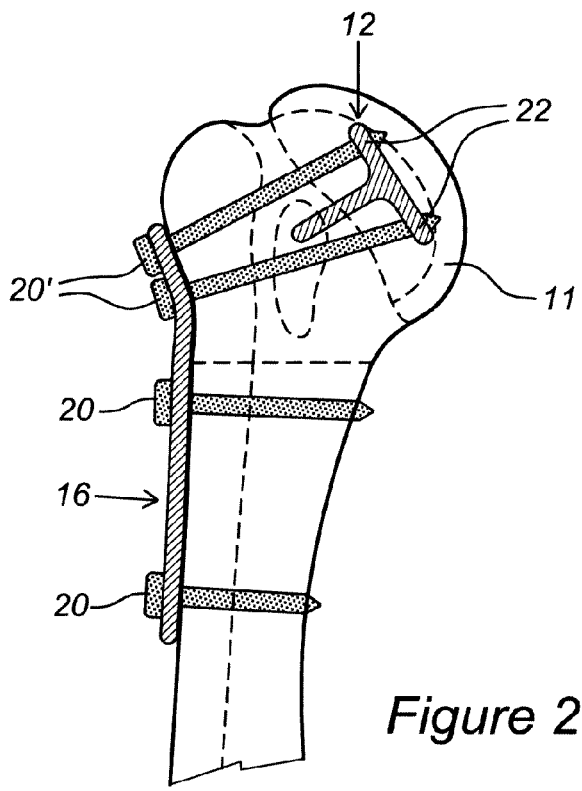

Step (d) of the present method, comprises locking the relative position of the articular supportive plate and said diaphyseal plate via one or more screws or pins, after correct reduction of the fractured bone fragments. The screws or pins (20') are sent via through holes in the proximal portion of the diaphyseal plate (16) and received by the pin receiving features of the articular supportive plate (12) (see FIG. 2d). In particular embodiments, one or more of the screws or pins which are sent via the through holes in the proximal portion of the diaphyseal plate may be received by the pin receiving feature(s) of the fin(s) of the articular supportive plate. To facilitate the procedure, the screws may be variable angle screws, or the through holes and pin receiving features of the proximal plate portion and articular supportive plate are provided with a bushing, a compression cap, or an expandable ring to lock the angular position of a screw.

Step (d) typically is performed after steps (a), (b) and (c) as described above. If the articular supportive plate comprises one or more fins, the fins may be pressed into the spongy bone (if still present in case of severe osteoporosis) under the articular surface of the humerus, pointing towards the centromedullar region of the diaphysis. In some cases, the humerus may comprise one or more cavities due to osteoporosis, which may accommodate the articular support plate and fin(s).

The pins and/or screws for locking the relative position of the articular supportive plate and the diaphyseal plate will typically also penetrate the bone fragments, thereby allowing for fixation of the various bone parts. Whereas locking plates alone typically require the use of relatively long screws which may perforate the caput humeri and cause damage to the glenoid cavity, the combination of the diaphyseal plate and articular supportive plate allows for the use of much shorter screws, thereby significantly reducing the risk of perforation and glenoid cavity damage. Moreover, the combination of a diaphyseal plate with an articular supportive plate provides an increased stability on the opposite side of the diaphysis, where typically no support is present from a diaphyseal plate due to difficulties in fixing such a plate to the inside of the arm. Accordingly, the combination of the diaphyseal plate and articular supportive plate may provide sufficient stability to proximal humeral fractures with metaphyseal comminution irrespective of varus or valgus deformity. This is in contrast with the use of a locking plate as such. Indeed, due to the typical position of the locking plate onto the lateral cortex of the humerus typically provides insufficient stability to proximal humeral fractures with a varus deformity.

Moreover, for the fixation of tuberosities, locking plates typically only allow for fixation parallel with the fracture lines (in a direction from the lateral to the medial side of the humerus). The combination of the diaphyseal plate, containment strips and fin(s) on the articular supportive plate described herein may further provide for fixation perpendicular to the fracture lines (in a direction from the anterior to the posterior side of the humerus and/or vice versa). This may provide a compensation for the forces of the rotator cuff. Indeed, the fin(s) (15) of the articular supportive plate (12) may allow for further stabilization of a tuberosity, by drilling one or more screws (20') through the tuberosity, wherein said screw is received by a pin receiving feature provided in a fin of the articular supportive plate (see FIGS. 3a and 3c). For further stabilization, the screw may be drilled into the tuberosity via a through hole provided in a containment strip (see further).

Figure 3A:
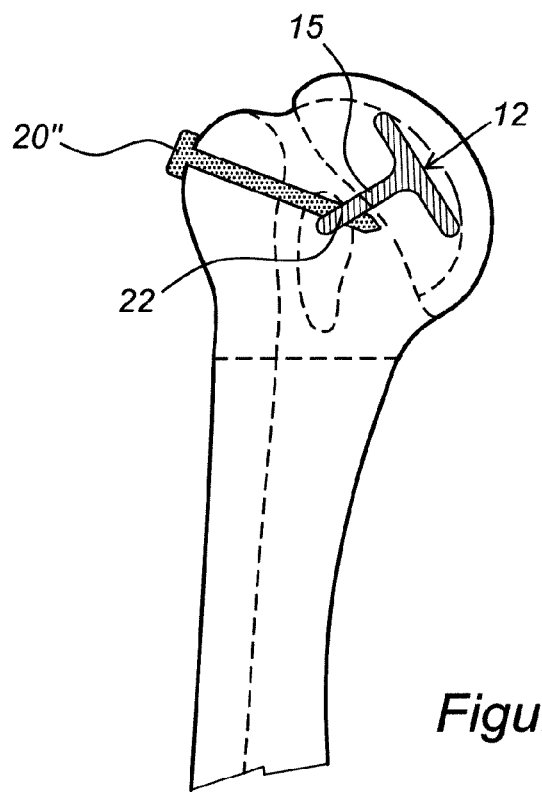
FIG. 3: Schematic view of the possibility of the fins (15) of the articular supportive plate (12) to receive screws (20') affixing the tuberosities (a) and b)), or of receiving screws (20") sent by a containment strip or plate (21) to surround each tuberosity in case of more comminuted fractures (c): frontal view, (d): lateral view).
Figure 3B:
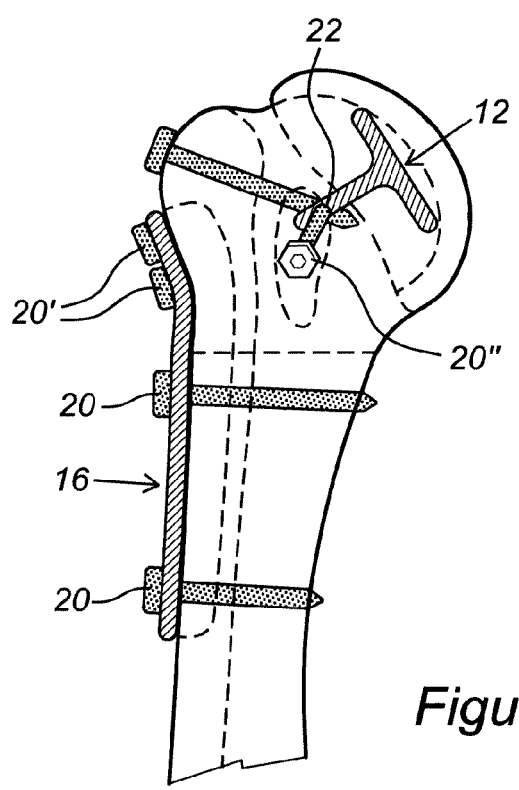
Figure 3C:
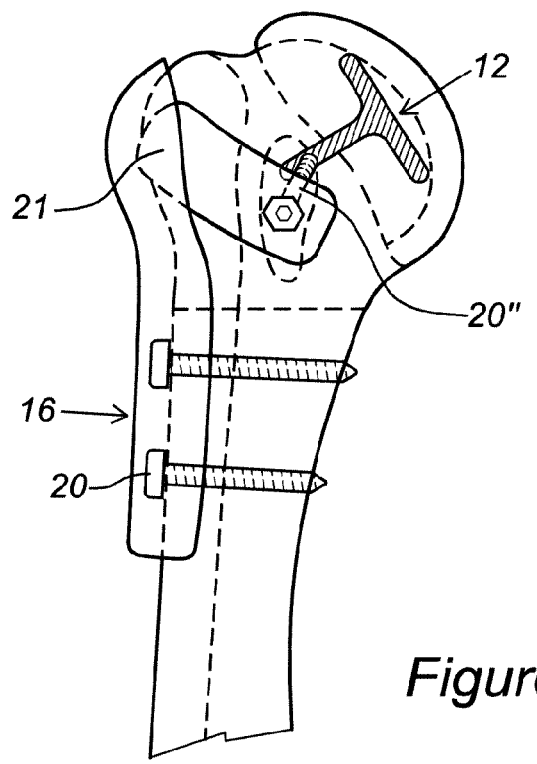
Figure 3D:
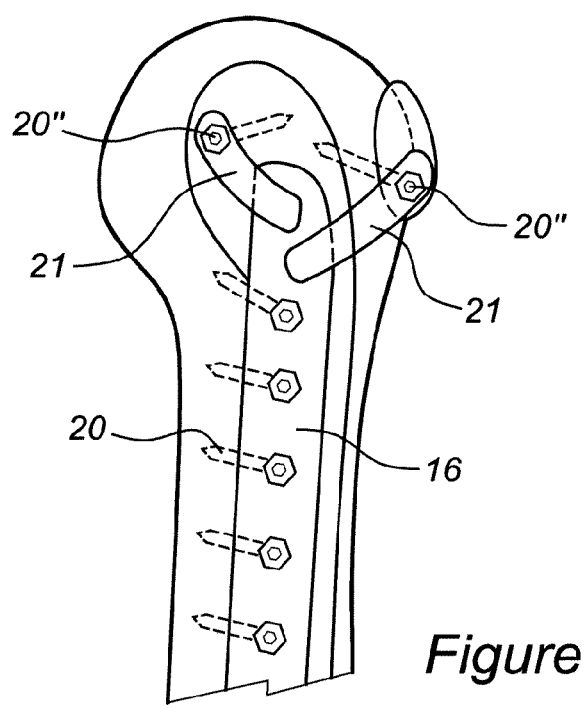

In optional step (e), one or more containment strips (21) as described above are coupled to the diaphyseal plate (16), preferably via the coupling features provided on the containment strips and the diaphyseal plate (see FIGS. 3c and 3d). The containment strips are then secured to one or more tuberosities of the humerus, for example via one or more screws or pins which are entered into the tuberosities via the through hole(s) provided in the containment strip. In particular embodiments, one or more of these screws or pins may be received by one or more through holes provided on the articular supportive plate or, preferably, the fin(s) thereof. If the containment strip is flexible or malleable, the shape of the containment strip may first be adjusted to the shape of the caput humeri prior to securing the containment strip.

The fixation of the tuberosities via containment strips coupled to a diaphyseal plate may provide more possibilities for fixation and may allow for the use of much shorter screws or pins compared to fixation of tuberosities via a locking plate only. Thus, the use of containment strips may further reduce the risk of perforation the caput humeri and the resulting damage to the glenoid cavity.

Postoperatively, the limb is typically immobilized, preferably with elbow close to the body. Gentle passive motion may be started after a few days.

The invention above was mainly illustrated and defined for fixing proximal humerus fractures, but can easily be adapted for use in other joint-fractures, such as those of the wrist, ankle, knee, or elbow. As a guidance, for each of these fractures, a number of features is provided in Table 1, which can be considered analogous in view of the present teachings.

The dimensions of the articular supportive plate and the containment strips and screws or pins as defined above may be hence be adapted to the dimensions of the bone anatomy of said fractures. In the following section, the use of the articular supportive plate and the osteosynthesis system or kit according to the present invention has been exemplified for use in said other types of fractures.

TABLE 1 overview of analogous elements of various joint fractures

| Fracture | Articular surface | Bone parts potentially stabilized by containment strip | Joint |
|---|---|---|---|
| Proximal Humerus | Caput humeri | greater tuberosity, lesser tuberosity | Shoulder |
| Distal Radius | Articular surface of distal radius | radial styloid process | Wrist |
| Distal Femur | Articular surface of distal femur | lateral condyle, medial condyle | Knee |
| Proximal Tibia | Articular surface of head of tibia | tibial tuberosity, lateral condyle, medial condyle | Knee |
| Distal Tibia | Cancellous bone of distal tibia | medial malleolus | Ankle |

Use of Osteosynthesis Device of the Invention for Repairing Ankle Fractures:
a) Distal Tibia Fracture Fixation An articular fracture of the distal tibia can also be repaired using the osteosynthesis device according to the present invention. The articular supportive plate would then have to be placed under the articular surface of the distal end of the tibia, whereby the fin(s) of the articular supportive plate project(s) towards the centromedullar axis of the tibia, i.e. away from the distal end of the tibia. Said articular supportive plate, supporting the subchondral bone of the pilon tibial, can receive screws or pins sent from a distal tibia diaphyseal plate alongside the shaft of the tibia. The medial malleolus can further be stabilized using containment plates as defined above.

Use of the Osteosynthesis Device of the Invention for Repairing Wrist Fractures:
a) Distal Radius Fracture Fixation.

When treating a radius fracture of the wrist, the articular supportive plate of the invention can be inserted in the articular surface of the distal radius. Fixing can be done for example using e.g. a juxta-articulate diaphyseal plate, sending screws or pins towards the inside of the distal radius, which can be received by the supportive plate placed inside the distal radius, The radial styloid can be further stabilized using containment plate variably attached to the diaphyseal plate as disclosed herein.

Use of the Osteosynthesis Device of the Invention for Repairing Fractures of the Knee:
a) Distal Femur Fracture Fixation.

For fixing a distal femur fracture, the articular supportive plate of the invention can be inserted under the articular surface of the distal femur, i.e. the lateral condyle, or the medial condyle, depending on the type of fracture. The articular supportive plate will then be able to receive screw or pins sent from an epicondylar plate. The fin(s) of the articular supportive plate again are orientated centromedullarly of the femur, i.e. pointing away from the condyles. Complex fractures again can be fixed with one or more containment plates that are attached to the diaphyseal plate.
b) Proximal Tibia Fracture Fixation.

For fixing a proximal tibia fracture, or a fracture of the upper part of the shin bone, the supportive plate of the invention can be inserted under the medial and/or lateral tibial plateau. As with proximal humerus fixation, the supportive plate can be placed under the articular surface of the tibial plateau. The fin(s) of the supportive plate will then typically be oriented in a centromedullar manner, projecting away from the tibial plateau. Said supportive plate then receives screws or pins sent from a diaphyseal plate placed alongside the tibia, pretty much similar to the situation exemplified above for proximal humeral fracture fixation. Further in similarity to the proximal humeral fracture fixation procedure, containment plates can be used to contain the condyles of the proximal tibia.

The invention claimed is:

1. Osteosynthesis device for articular fracture fixation, comprising an articular supportive plate for supporting the articular surface of a long bone, said articular supportive plate comprising: a first side, oriented centromedullarly facing the cancellous bone and a second side facing or supporting the articular surface, said first side comprising:
   at least one pin receiving feature for receiving a pin or a screw; and
   at least one fin attached to or attachable to said articular supportive plate;
wherein, when attached to said articular supportive plate, said fin projects from said first side of said articular supportive plate, said fin further being provided with a plurality of pin receiving features for receiving a pin or screw; and
wherein said one or more pin receiving features of said articular supportive plate are configured to receive a variable angle locking screw.

2. The osteosynthesis device according to claim 1, wherein said pin receiving features provided on said fin comprise:
   a plurality of holes; and/or
   a plurality of upstanding fingers protruding from said fin.

3. The osteosynthesis device according to claim 1, wherein said pin receiving features provided on said articular supportive plate comprise a plurality of upstanding fingers protruding from said supportive plate, and/or comprise a plurality of through holes or cells.

4. The osteosynthesis device according to claim 1, wherein one edge of said articular supportive plate is further provided with an upstanding tab.

5. The osteosynthesis device according to claim 1, wherein said articular supportive plate has outer dimensions of between about 2 and 5 cm, preferably between 2 and 3 cm, and/or can have a thickness of between about 1 and 5 mm, preferably between about 1 and 4 mm, more preferably between about 1 and 3 mm.

6. The osteosynthesis device according to claim 1, wherein said articular plate has a meshed structure.

7. The osteosynthesis device according to claim 1, wherein said articular supportive plate comprises:
   one fin attached to or attachable to said articular supportive plate wherein, when attached to said articular supportive plate, said fin projects from said plate; or
   two or more fins attached to or attachable to said articular supportive plate wherein, when attached to said articular supportive plate, said fins project from said plate.

8. Use of the device according to claim 1, for repairing a fracture selected from the group consisting of: the proximal humerus, the distal radius, the proximal or distal tibia, and the distal femur.

9. A kit comprising the osteosynthesis device according to claim 1, and further comprising a diaphyseal plate, said diaphyseal plate comprising:
   a longitudinal distal plate portion provided with at least one through hole for securing said diaphyseal plate to the shaft of the bone; and
   a proximal plate portion provided with at least one through hole, wherein said through hole of said proximal plate portion and at least one of said holes of said articular supportive plate or fin are configured to respectively send and receive the same screw or pin.

10. The kit according to claim 9, further comprising at least one containment plate provided with one or more through holes, wherein said containment plate and said proximal plate portion each comprise a coupling feature for coupling said containment plate to said proximal plate portion.

11. The kit according to claim 9, wherein said coupling features provide a rail system, and/or an adjustable attachment means.

12. The kit according to claim 9, wherein said containment plate is flexible or malleable.

13. The kit according to claim 9, wherein said articular supportive plate and said diaphyseal plate are formed of one or more materials selected from the group consisting of titanium, titanium alloy, cobalt-chromium alloy, stainless steel, tantalum, tantalum alloy, polyethylene, polyether ether ketone (PEEK), poly(lactic acid), poly(D-lactic acid), poly (L-lactic acid), poly(glycolic acid), poly(e-caprolactone), poly(dioxanone), poly(lactide-coglycolide), poly(propylene fumarate) (PPF), oligo(poly(ethylene glycol) fumarate), poly(glycolide-co-trimethylene carbonate), a polyorthoester, and a polyanhydride.

14. The kit according to claim 9, further comprising at least one screw, said screw being cuttable or breakable.

15. Method of fixating an articular fracture in a long bone using the kit according to claim 9, said method comprising:
  (a) mounting of said articular supportive plate under the articular surface of the proximal or distal end of the long bone;
  (b) securing said diaphyseal plate to the shaft of the long bone;
  (c) reducing the fracture;
  (d) locking the relative position of said articular supportive plate and said diaphyseal plate via one or more screws or pins; and
  (e) optionally, coupling one or more containment plates onto said diaphyseal plate, and securing said containment strips onto said distal or proximal end of the long bone.

16. The method according to claim 15, for use in repairing a fracture selected from the group consisting of: the proximal humerus, the distal radius, the proximal or distal tibia, and the distal femur.

* * * * *